United States Patent
Marikovsky

(10) Patent No.: US 6,740,681 B1
(45) Date of Patent: May 25, 2004

(54) PHARMACEUTICAL COMPOSITIONS COMPRISING THIRAM

(75) Inventor: Moshe Marikovsky, Mazkeret Batya (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 09/600,001

(22) PCT Filed: Jan. 11, 1999

(86) PCT No.: PCT/IL99/00018

§ 371 (c)(1),
(2), (4) Date: Jul. 10, 2000

(87) PCT Pub. No.: WO99/34763

PCT Pub. Date: Jul. 15, 1999

(30) Foreign Application Priority Data

Jan. 11, 1998 (IL) .................................................. 122891

(51) Int. Cl.⁷ .............................................. A61K 31/16
(52) U.S. Cl. ...................................................... 514/599
(58) Field of Search ........................................ 514/599

(56) References Cited

U.S. PATENT DOCUMENTS 5,716,981 A * 2/1998 Hunter et al.

FOREIGN PATENT DOCUMENTS

| EP | 0 284 879 | 10/1988 |
| WO | 95 30415 | 11/1995 |

OTHER PUBLICATIONS

Koch et al., Nature 1995:376:517–519.*
Staal–van den Brekel et al., Virchows. Arch. 1996;428: 21–27.*
Goss et al., Anticancer Drugs, 1996; 7: 363–385.*
VCAM–1/CD106 Mini Review printed in R&D Systems' 1997 Catalog.*
M. Takaishi, "Inhibition of spontaneous leukemia in F–344 rats by tetramethylthiuram disulfide," Gann, vol. 74, No. 6, 1983, pp. 810–813.
G. Weber, "Neue systemische Therapie der Psoriasis", Hautzart, vol. 36, No. 1, 1985, pp. 20–24.
B.S. Warren, "Mechanisms of inhibition of tumor progression," Basic Life Sci., vol. 61, 1993, pp. 279–289.
G.Y. Liu, "Induction of apoptosis by thiuramdisulfides, the reactive metabolites of dithiocarbamates, through coordinative modulation of NFkB,c–fos/c–jun, and p53 proteins," Mol. Carcinogen, vol. 22, No. 4, 1988, pp. 235–246.

(List continued on next page.)

Primary Examiner—Sreeni Padmanabhan
Assistant Examiner—San-ming Hui
(74) Attorney, Agent, or Firm—Browdy and Neimark

(57) ABSTRACT

Thiram (tetramethyliuram disulfide) is shown to inhibit angiogenesis and/or inflammation and to be useful in the treatment of angiogenesis-dependent disorders, including neoplasms, and in the inhibition, treatment and allevation of inflammation associated with several disorders and diseases, such as rheumatoid arthritis. Thiram is further useful for prevention of cell hyperproliferation and formation of clots along or around medical devices.

14 Claims, 6 Drawing Sheets

OTHER PUBLICATIONS

D.J. Stewart, "Phase I study of the combination of disulfiram with cisplatin", Am. J. Clin. Oncol., vol. 10, No. 6, 1987, pp. 517–519.

H.K.A. Schirmer, "Disulfiram and tumor inhibition," Transactions of the American Association of Genitourinary Surgeons, vol. 58, 1966, pp. 63–66.

G.N. Hannan, "Regulation of polypeptide synthesis in endothelial cells and hybridoma cells by the copper ionophore disulfiram," Cell Biol. Int. Rep., vol. 6, No. 5, 1982, pp. 423–432.

Elskens et al., "In vitro inactivation of yeast glutathione reductase by tetramethylthiuram disulphide", Eur. J. Biochem., vol. 231, pp. 667–672, (1995).

George et al., "Studies on clastogenic and carcinogenic potency of tetramethyl thiuram disulphide", Cancer Letters, vol. 97, pp. 213–216, (1995).

Hasegawa et al., "Carcinogenicity Study of Tetramethylthiuram Disulfide (Thiram) in F344 Rats", Toxicology vol. 51, pp. 155–165, (1988).

Maita et al., "Chronic Toxicity Studies with Thiram in Wistar Rats and Beagle Dogs", Fundamental and Applied Toxicology, vol. 16, pp. 667–686, (1991).

Perocco et al., "Toxic and DNA–Damaging Activities of the Fungicides Mancozeb and Thiram (TMTD) on Human Lymphocytes in Vitro", teratogenesis, Carcinogenesis, and Mutagenesis, vol. 9, pp. 75–81, (1989).

Sanny et al., "Inactivation of horse liver mitochondrial aldehyde dehydrogenase by disulfiram", Biochem. J., vol. 242, pp. 499–503, (1987).

Takahashi et al., "Inhibitions of Spontaneous Leukemia in F–344 Rats by Tetramethylthiuram Disulfide (Thiram)", Gann, vol. 74, pp. 810–813, (1983).

* cited by examiner

FIG. 1A  control (saline)
FIG. 1B  FGF (10ug)
FIG. 1C  T (60ug)
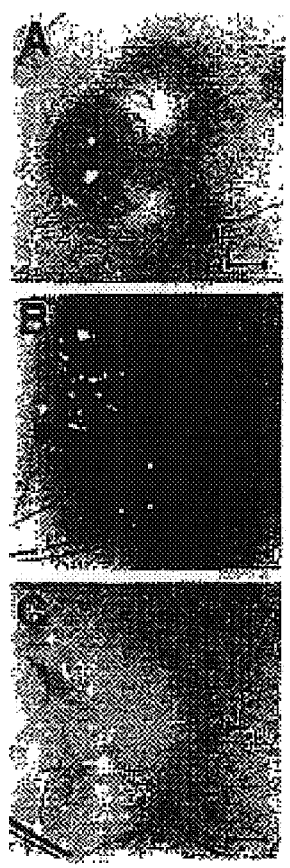

PHARMACEUTICAL COMPOSITIONS COMPRISING THIRAM

CROSS REFERENCE TO RELATED APPLICATION

The present application is the national stage under 35 U.S.C. 371 of PCT/IL99/00018, filed Jan. 11, 1999.

FIELD OF THE INVENTION

The present invention relates to the use of thiram as an inhibitor of angiogenesis and/or inflammation for the preparation of pharmaceutical compositions useful for the treatment of angiogenesis-dependent disorders and/or inflammation associated with a disease or disorder, and to methods of treatment of said disorders.

BACKGROUND OF THE INVENTION

Tetramethylthioperoxydicarbonic diamide or tetramethylthiurarn disulfide, hereinafter thiram, is a fungicidal and bactericidal agent used as antiseptic, seed disinfectant and animal repellent. It is also used in the rubber processing industry as rubber accelerator and vulcanizer. Thiram has an ampiphilic nature, is soluble in water but it solubilizes better in hydrophobic solutions such as methanol, acetone or chloroform.

Thiram was shown to inhibit various enzymes in vitro such as yeast glutathione reductase (Elskens, 1995) and horse liver mitochondrial aldehyde dehydrogenase (Sanny, 1987), and in vivo such as lipoprotein lipase activity in adipose tissue (Sadurska, 1993), aldehyde dehydrogenase and aldehyde oxidase (Freundt, 1977) in rats.

Thiram was shown to be toxic to human lymphocytes in vitro in the presence of the S-9 mix (Perocco, 1989). Thiram was also shown to reduce the incidence of spontaneous leukemia and of pituitary and thyroid tumors in rats treated for two years (0.05–0.1% in the diet), without being carcinogenic (Takahashi, 1983; Hasegawa, 1988). Female rats treated with 40 mg/Kg/day for 2 years with thiram had decreased spontaneous occurrences of mammary fibroadenoma (Maita, 1991). Thiram also decreased the formation of N-nitrosodiethylamine-induced hepatomas in rats (Klimova, 1990).

Thiram was shown to be non-clastogenic (100–200 mg/Kg) and non-carcinogenic in the skin (1 mg) in male Swiss albino mice (George, 1995).

None of the above publications describes or suggests the use of thiram as an inhibitor of angiogenesis and/or of inflammation.

SUMMARY OF THE INVENTION

It has now been found in accordance with the present invention that thiram inhibits angiogenesis and is able to block neovascularization induced subcutaneously in nude mice. It has further been found that thiram reduced inflammation in rats suffering from adjuvant arthritis.

The pharmaceutical composition of the invention is suitable for treatment of angiogenesis-dependent diseases including, but not being limited to, ophthalmologic disorders such as diabetic retinopathy, corneal graft neovascularization, neovascular glaucoma, trachoma and retinopathy of prematurity also known as retrolental fibroplasia, dermatologic disorders including dermatitis, psoriasis and pyogenic granuloma, cardiovascular disorders including atherosclerosis, pediatric disorders including hemangioma, angiofibroma, and hemophilic joints, neurologic cerebrovascular disorders including arteriovenous malformation, neoplasms including leukemia and solid tumors, connective tissue disorders including arthritis and scleroderma, autoimmune diseases and treatment of hypertrophic scars.

The solid tumors that can be treated with thiram according to the invention include, but are not limited to, bladder, breast, cervix, ear, esophagus, kidney, larynx, liver, lung, ovary, pancreas, prostate, skin, stomach, thyroid, urethra and uterus cancers.

The pharmaceutical composition of the invention is further suitable for the inhibition, alleviation or treatment of inflammatory symptoms associated with, for example, rheumatic diseases such as rheumatic fever and rheumatoid arthritis, fibrositis, myositis, neuritis, sciatica, lumbago, glomerulitis, nephritis, vasculitis, allergic diseases and autoimmune diseases.

For the preparation of the pharmaceutical compositions of the invention, thiram is mixed with pharmaceutically acceptable carriers and conventional excipients to produce unit dosage formulations suitable for administration. Any suitable mode of administration is envisaged by the invention, but oral administration is preferred.

The dosage of thiram to be administered daily will depend on the disorder being treated and the age, weight and condition of the patient being treated, and can be determined without difficulty by skilled physicians. Based on the examples herein in animals, it can be deduced that dosages between 1–50 mg/person are suitable for humans.

In another aspect, the invention relates to a method for inhibiting angiogenesis and/or inflammation in a mammal, particularly humans, which comprises administering to a mammal in need thereof an amount of thiram effective for inhibiting angiogenesis and/or inflammation.

In still another aspect, the invention relates to the use of thiram to prevent cell hyperproliferation and formation of clots along or around medical devices such as stents, catheters, cannulas, electrodes, and the like. In one embodiment, thiram may be systemically administered to a patient in which such a device has been inserted. In another embodiment, the medical device is coated with thiram before insertion in the patient, and such thiram-coated medical devices are also envisaged by the present invention.

Abbreviations: BCE: bovine capillary endothelial cells; bFGF: basic fibroblast growth factor; BSMC: bovine vascular smooth muscle cells; DMEM: Dulbecco's Modified Eagle's Medium; EGF: epidermal growth factor; FCS: fetal calf serum; GPS: glutamine/penicillin/streptomycin; HB-EGF: heparin-binding epidermal growth factor.

BRIEF DESCRIPTION OF THE DRAWINGS

FIGS. 1A–1C show inhibition of neovascularization in nude mice by thiram (T). Agarose beads containing the angiogenic compound bFGF (10 µg/bead) were implanted subcutaneously in nude mice and the angiogenic potential of bFGF in vivo was demonstrated 4 days after implantation, in skin specimens (FIG. 1B). Saline, as a negative control, did not induce neovascularization around the bead (FIG. 1A). Thiram (T) introduced systemically at 60 µg/mouse inhibited almost completely neovascularization induced by bFGF inside and around the bead (FIG. 1C). Bar is one mm.

DETAILED DESCRIPTION OF THE INVENTION

Figure 2A:
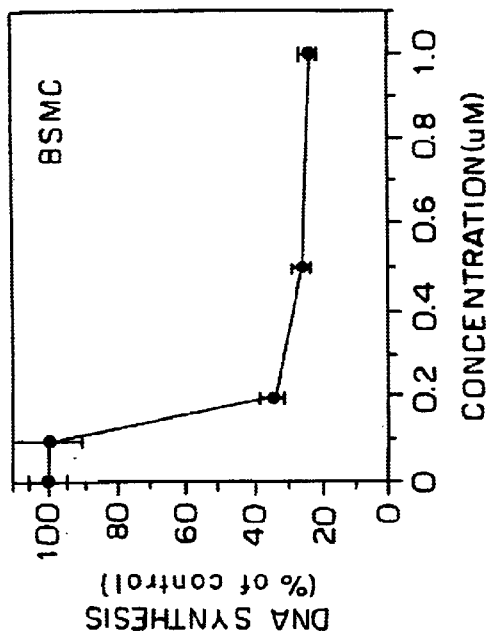
FIGS. 2A–2D show in vitro inhibition of DNA synthesis by thiram in a dose-dependent manner in BCE, BSMC, BALB/MK and C6 rat glioma cells, respectively, as measured by incorporation of $^3$H-thymidine into the cells. Experiments were done in triplicates and the inhibition was calculated as percentage of DNA synthesis of non-treated control.

Vascular smooth muscle cells and endothelial cells are the two cell types constituting the blood vessel walls. Angiogenesis, the growth of new capillary blood vessels by sprouting from established vessels, requires the growth of vascular endothelial cells and vascular smooth muscle cells. According to the data of the present invention, thiram is clearly identified as an effective inhibitor of angiogenesis.

Thus, as shown herein, thiram inhibited in vivo the induction of new blood vessels in the mouse skin and was effective when administered orally. The ability of thiram to inhibit at low concentrations the growth of cultured bovine capillary endothelial (BCE) cells suggests that the drug acts directly on capillary endothelial cells. Moreover, the inhibition of endothelial cell growth was shown to be non-reversible. The growth of bovine vascular smooth muscle cells (BSMC), another cell constituent of the blood vessel wall, was also inhibited by thiram at low concentrations (0.2–0.5 $\mu$M). The fact that thiram induces apoptosis in capillary endothelial cells and fails to induce apoptosis in other cell types such as vascular smooth muscle cells, keratinocytes (MK), fibroblasts and C6 rat glioma cells, indicates that it has some specificity for capillary endothelial cells. Indeed, when thiram was administered systemically at low doses of 25–60 $\mu$g/mouse, the formation of new blood vessels was specifically disrupted, while no evidence for damage in other tissues was observed. The low concentration of thiram administered systemically when calculated for the volume of a mouse (3 $\mu$M), was in the range of that used in vitro for endothelial cells (0.1–0.2 $\mu$M), especially when the metabolic processing of the drug in the body is taken into account.

As might be expected from its ability to inhibit capillary endothelial cells and BSMC at concentrations achievable in vivo, systemic treatment of mice with thiram inhibited neovascularization in the skin. The growth of C6 rat glioma cells in vitro was inhibited by thiram. Taken together with the fact that active angiogenesis is essential for the progressive growth of solid tumors (Folkman, 1990) and that C6 glioma tumor development is angiogenesis-dependent (Abramovitch, 1995; Ikeda, 1995; Niida, 1995; Plate, 1992), one could expect that C6 glioma tumor growth would be affected by thiram. Indeed, thiram significantly reduced C6 tumor development in vivo when administered systemically per os at low concentrations similar to those observed to be effective in vitro, both for endothelial and C6 glioma cells, suggesting that the inhibitory activity for C6 glioma tumor growth is induced through inhibition of angiogenesis and of C6 glioma cell growth. The mechanism through which thiram induces its inhibitory effects in vitro or in vivo is not known. Also the reason for capillary endothelial cells being more liable to thiram than other cell types for induction of apoptosis, is not known.

The results shown here demonstrate that thiram inhibits capillary endothelial and vascular smooth muscle cell growth and induces apoptosis in capillary endothelial cells, and that, when used systemically in mice, thiram inhibits angiogenesis and decreases C6 glioma tumor growth, and clearly define thiram as a new inhibitor of angiogenesis and show its potential use for therapy in angiogenesis-dependent diseases such as pathologies in which neovascularization is involved, including neoplasia.

Adjuvant arthritis is an experimental disease inducible in some strains of rats by immunizing them to antigens of *Mycobacterium tuberculosis* (Pearson, 1956). The disease is thought to be a model of rheumatoid arthritis in humans (Pearson, 1964). The alleviation of inflammation and inhibition of adjuvant arthritis in rats indicate that thiram can be used for inhibition, treatment and alleviation of inflammation associated with several diseases, conditions or disorders.

The invention will now be illustrated by the following non-limiting examples.

EXAMPLES

Material and Methods (a) Materials:

Thiram (Sigma) and mouse EGF (Collaborative Biomedical Products, Bedford, Mass., USA) were purchased. Recombinant b-FGF and recombinant HB-EGF were kindly provided by Prof. Gera Neufeld, and by Dr. Judith A. Abraham (Scios Nova Inc., Mountain View, Calif.), respectively.

(b) Cell Lines:

C6 rat glioma cells were routinely cultured in DMEM supplemented with 5% FCS (Biological Industries, Israel), GPS (100 U/ml penicillin, 100 mg/ml streptomycin (Biological Industries, Israel) and 2 mM glutamine (Biolab Ltd. Israel)) and 125 μg/ml fungizone (Biolab Ltd, Israel).

Brain bovine capillary endothelial cells (BCE) and bovine vascular smooth muscle cells (BSMC), kindly provided by Prof. Israel Vlodavsky (Hadassah Medical School, Jerusalem, Israel), were cultured at 37° C. in low glucose DMEM (1 g/liter) supplemented with 10% calf serum (HyClone, Logan, Utah, USA), a serum-free supplement: biogro-1 (Beth Haemek, Israel) and GPS.

Bovine aortic vascular smooth muscle cells (BSMC) were cultured in low glucose DMEM (1 g/liter) supplemented with 10% FCS (HyClone, Logan, Utah) and GPS.

The BALB/MK epidermal keratinocyte cell line, kindly provided by Dr. S. Aaronson (National Cancer Institute, Bethesda, Md., USA), was cultured (37° C., 10% $CO_2$ humidified atmosphere) in calcium-free MEM (Beth Haemek, Israel) supplemented with 10% dialyzed FCS and murine EGF (5 ng/ml).

(c) Measurement of DNA Synthesis

C6 rat glioma cells were plated in 96-well plates (Nunc, Denmark) (5000 cells per well) in DMEM with 5% FCS. After 6 hours the cells were rinsed and incubated for 48 hours in serum free medium. 5% FCS or growth factors were then added to the cells for 24 hours (triplicates). $^3$H-methyl-thymidine (5 μCi/ml) (Rotem Ind. Ltd., Israel) was added to the cells for the last 14 hours. The cells were rinsed with 100 μl methanol for 10 minutes, followed by 200 μl 5% trichloroacetic acid, and then rinsed and lysed with 150 μl 0.3M NaOH. Radioactive thymidine incorporated into the DNA was determined for 1 min with 3 ml scintillation liquid (ULTIMA GOLD Packard) in a β-counter. DNA synthesis assays were performed in triplicates.

Bovine capillary endothelial cells (BCE) and bovine aortic BSMC were plated in 24-well plates (6000 cells per well) in 500 μl DMEM medium supplemented with 10% Colorado calf serum (CCS) (GIBCO, USA) and GPS. After 24 hours, medium was changed to starvation medium (2% CCS, 0.5% BSA, GPS) for 24 hours. $^3$H-methyl-thymidine (5 μCi/ml) was added for the last 6 hours. DNA synthesis assays were performed as described above, in triplicates. DNA synthesis assays in BALB/MK keratinocytes were performed as previously described (Marikovsky, 1995). DNA synthesis assays were performed in triplicates.

Thiram was prepared in 0.1 mM stock solutions in DMSO. Control samples were incubated with the appropriate concentration of DMSO. Inhibition was calculated as percentage of DNA synthesis of control.

(d) Subcutaneous Angiogenesis in Nude Mice

Spherical agarose beads of approximately 1 mm in diameter were formed from 4% low gelling temperature agarose (Sigma) in PBS containing b-FGF or HB-EGF as angiogenic agent. The candidate angiogenic agent (10 μg/bead) was warmed in sterile microtest tubes to 40° C. in a dry-bath for a few seconds. 10 μl of agarose solution (6% in saline, 45° C.) were then added to 5 μl of the angiogenic compound and beads were formed above ice using a 20 μl pipette tip. Beads were implanted subcutaneously 1 cm away from the incision site as reported previously for multicellular spheroids (Abramovitch, 1995) in mice anesthetized with a single dose of 75 mg/kg ketamine+3 mg/kg xylazine (i.p.). Experiments were carried out for 4 days in CD1 nude male mice. Each day one ml of aqueous solutions with or without 0.1–0.25 mM (25–60 μg) thiram was introduced per os to the mice using a feeding needle. Treatment was for three days starting from the day of bead implantation until one day before termination. Experiments were done in quadruplicates and repeated three times.

(e) Growth of C6 Glioma Tumors

C6 rat glioma cells ($10^6$) were injected subcutaneously into the back of the neck of CD1 nude male mice. After 3 days, 1 ml of aqueous solutions with or without 0.1–0.5 mM thiram (25–120 μg) was introduced per os to the mice using a feeding needle. Mice were orally fed three times per week. Tumors were removed 30 days following C6 cells injection, weighed, fixed in buffered formalin and histological sections were prepared. Each experimental group included 8 animals, and experiments were repeated twice.

(f) Analysis of Apoptotic Cells by FACS

Cells were cultured in plastic tissue culture dishes for 48 hours in presence of growth media as described above, until reaching 40–50% confluency. Thiram was then added to the cells for 20 hours. The cells were removed from the plates by EDTA-trypsin and fixed in ice-cold 70% ethanol (BioLab, Israel) in −20° C. for 2 hr to overnight. The fixed cells (2–5×$10^6$) were washed once with HEPES-buffered saline (HBSS) and incubated with 0.5 mg/ml RNAseH (Boehringer Mannheim). Afterwards the cells were resuspended in HBSS containing 50 μg/ml propidium iodide (Sigma) and subsequently analyzed on a FACSort flow cytometer (Beckton Dickinson Inc.) using Lysis II software. For the analysis, 10,000 cells were examined from each sample. The percentage of the hypodiploid cells was measured (Darzynkiewicz, 1992; Afanasyev, 1993). The cell cycle histogram was divided into four regions according to the cell cycle phases: Ap, apoptotic cells; $G_1$, diploid cells; S, intermediate cells; and $G_2$/M, tetraploid cells.

(g) TUNNEL Assay for Apoptosis

Cells were cultured on microscope slides for 48 hours in presence of growth media as described above, until reaching 40–50% confluency. Thiram was then added to the cells for 6 hours or for 20 hours in the case of BALB/MK keratinocytes, fixed with 4% paraformaldehyde and washed three times with PBS. Apoptosis was analyzed by the in situ TUNEL staining carried out as described (Wride, 1994). Briefly, microscope slides were incubated for 15 min in 2×SSC buffer at 60° C., washed in DDW and incubated with 20 μg/ml proteinase K (Boehringer Mannheim) for 15 min at room temperature. After a wash with DDW, endogenous peroxidases were inactivated by incubating the slides with 2% $H_2O_2$ in PBST (PBS with 0.05% Tween 20) for 10 min at room temperature. Slides were then incubated in TdT buffer (Boehringer Mannheim) for 5 min at room temperature, and a reaction mixture containing 5×TdT buffer and 1 μl biotin-21-dUTP (Clontech, 1 mM stock) and 8 units of the TdT enzyme (Boehringer Mannheim) in total volume of 50 μl was subsequently added. The reactions were carried out at 37° C. for 1.5 hr in a humid chamber. The slides were washed in 2×SSC, DDW and finally with PBS and covered with 10% skim milk in PBST for 15 min. After removal of the skim milk, the sections were incubated with ABC solution from ABC kit (Vector Laboratories, Inc.) for 30 min at room temperature, washed with PBS and stained using AEC procedure (Sigma) The slides were then washed ×3 in DDW and stained with haematoxylin for 30 sec and mounted by Kaiser's glycerol gelatin (Merck).

(h) Growth of Lewis Lung Carcinoma Tumors

The Lewis lung carcinoma (3 LL), which originated spontaneously in a C57/BL/6J(H-$2^b$) mouse, is a malignant tumor that produces spontaneous lung metastases. The metastatic clone D122, kindly provided by Prof. Lea Eisenbach (Weizmnann Institute of Science, Rehovot, Israel), was used herein for tissue culture and for in vivo experiments. The cell cultures were maintained in DMEM supplemented with 10% heat-inactivated FCS, glutamine, antibiotics, sodium pyruvate and nonessential amino acids.

To determine the development of a tumor from a metastatic foci, the i.v. model was used as previously described (Eisenbach, 1983). Briefly, D122 cells ($5 \times 10^5$) in PBS were injected i.v. to the tail of C57/B1 male mice and after 24 days mice were killed by injecting 20 μg/mouse xylazine (i.p.) and their lungs weighed. Three days following D122 tumor cells injection, mice were treated per os with thiram or saline 3 times per week. Each experimental group included 8 animals, and experiments were repeated twice.

(i) Inhibition of Adjuvant Arthrithis in Rats

*Mycobacterium tuberculosis* (MT) H37 RA was injected to the tail of 9–10 week old Lewis female rats to induce adjuvant arthritis AA). Inflammation was assessed by the number of inflamed joints in all four limbs in a double blind test and scored on a scale of 0 (no arthritis) to 16 (full arthritis). Treatment with 140 or 280 μg thiram/rat three times per week began 3 days following MT injection, and assessment of inflammation started 13 following MT injection.

Example 1

In vivo Inhibition of Neovascularization by Thiram

Agarose beads containing the angiogenic factor bFGF (10 μg/bead) were implanted subcutaneously into CD1 nude mice as described in section (d) of "Materials and Methods" above. The results are shown in FIG. 1. After 4 days new blood vessels clearly developed around and inside the beads containing bFGF (FIG. 1B) while the control beads containing only saline appeared clear and without any new blood vessels being formed around or within the beads (FIG. 1A). However, when the mice were daily fed per os during 3 days with 1 ml aqueous solution (0.1–0.25 mM) of thiram (T) (25–60 μg/mouse/day), angiogenesis around the beads containing bFGF was clearly inhibited (FIG. 1C).

Example 2

Thiram Inhibits Capillary Endothelial Cell Proliferation

Figure 2B:
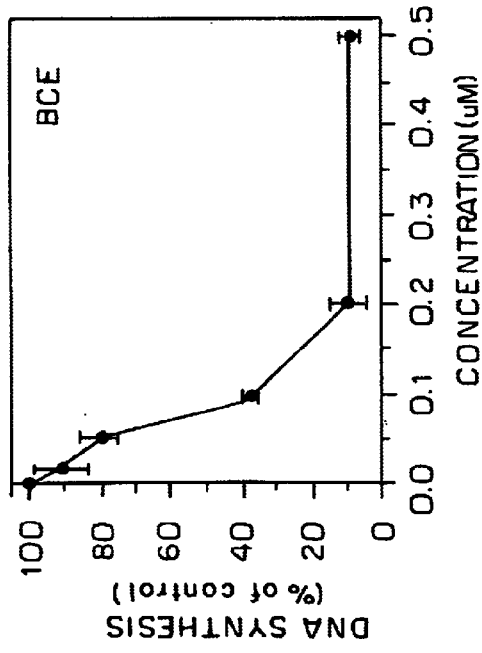
Figure 2C:
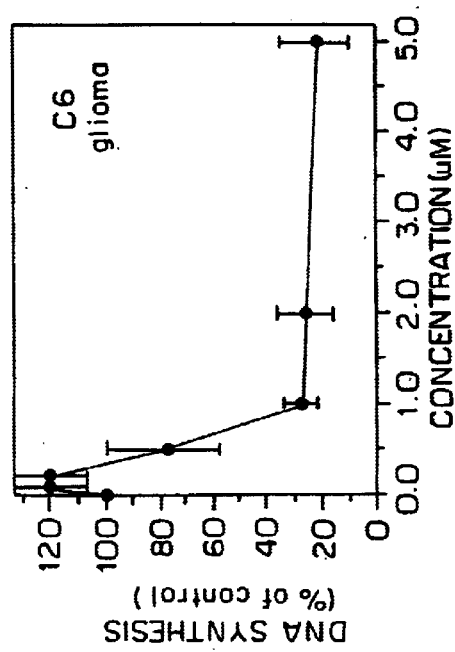

To determine whether thiram acts directly on endothelial cells rather than on accessory cells such as macrophages and mast cells that can be responsible for the development of an angiogenic response in vivo, the effect of the drug on the growth of BCE cells was examined in vitro as described in section (c) of "Materials and Methods" above. DNA synthesis in BCE cells was measured in presence of increasing concentrations of thiram incubated for 24 hours with the cells. The results are shown in FIG. 2. At concentrations ranging from 50 nM-0.5 μM, disulfiram was able to inhibit DNA synthesis in BCE cells in a dose dependent manner, complete inhibition being achieved at 0.2 μM thiram (FIG. 2A). BCE cells were shown to be more sensitive to the inhibitory activity of disulfiram than other cell types such as BALB/MK keratinocytes (FIG. 2C), C6 rat glioma cells (FIG. 2D) or bovine aortic vascular smooth muscle cells (BSMC) (FIG. 2B). Maximal inhibitory activity (80%) for BSMC was at 0.5–1 μM thiram, while maximal inhibitory activity for C6 glioma cells or BALB/MK keratinocytes was at concentrations 10 fold higher (2–3 μM) than those for endothelial cells (0.2 μM). At higher concentrations (>10 μM), thiram became less inhibitory for all cell types examined (not shown).

Figure 2D:
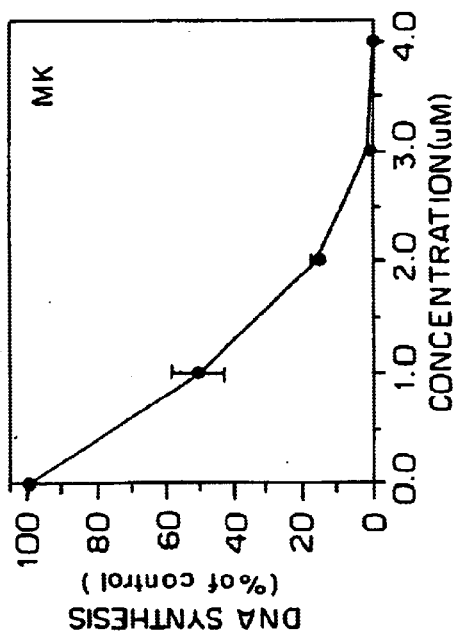
Figure 3A:
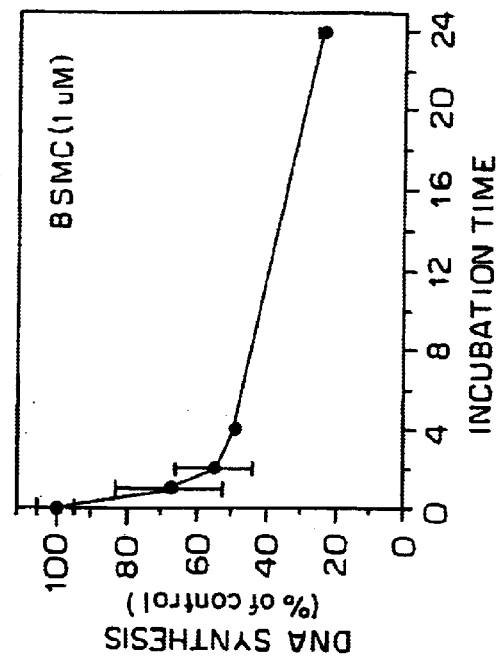
FIGS. 3A–3D show inhibition of DNA synthesis in a non-reversal manner by thiram at various periods of time (1, 2, 4 and 24 hours) in BCE, BSMC, BALB/MK and C6 rat glioma cells, respectively, as measured by the incorporation of $^3$H-thymidine into the cells. Experiments were done in triplicates and the inhibition was calculated as percentage of DNA synthesis of non-treated control.
Figure 3B:
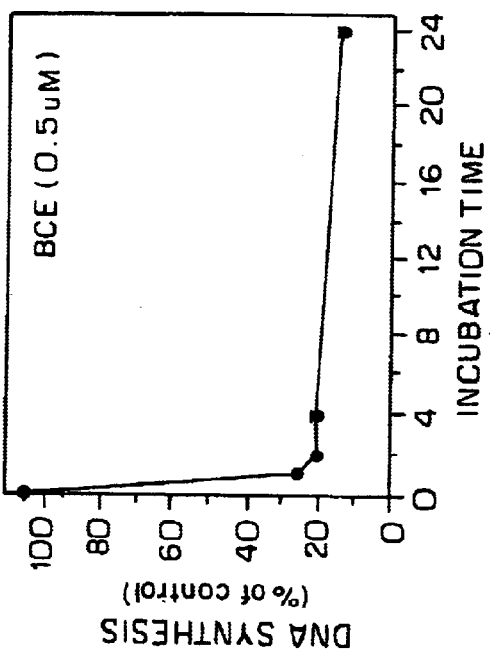
Figure 3C:
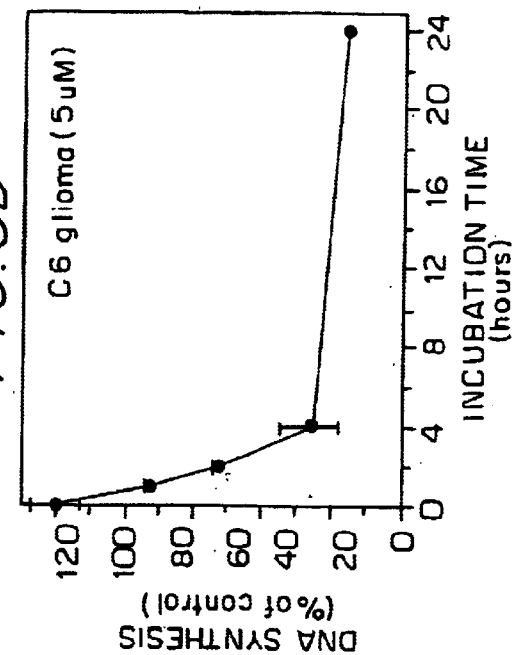
Figure 3D:
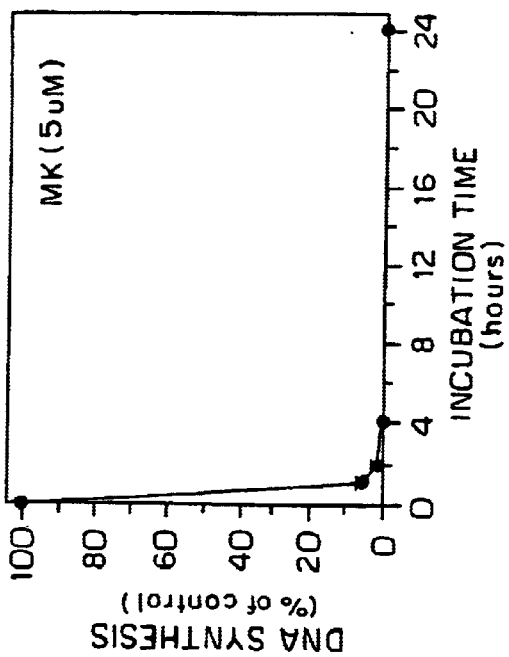

To examine the time course of the effect of thiram and whether the effect was reversible, cells were incubated with thiram for various periods of time (1, 2, 4 and 24 hours), then washed away and DNA synthesis was determined. One to 4 hours of exposure to thiram were enough to induce maximal inhibitory effect at concentrations ranging from 0.5 μM for BCE cells (FIG. 2A) to 5 μM for BALB/MK keratinocytes (FIG. 3C) and C6 glioma cells (FIG. 2D). As shown, for BCE, MK and C6 glioma cells the inhibitory effect seemed to be maintained even 24 hours following short exposure to the drug. BCE cells were most sensitive: 1–2 hours of incubation with as low as 0.5 μM thiram were enough to induce near maximal inhibition of DNA synthesis (FIG. 2A). BSMC were less sensitive as far as time course is concerned when incubated with 1 μM thiram. Following 4 hours of incubation with 1 μM thiram, DNA synthesis inhibition in BSMC reached only 50% (FIG. 3B). The data shown here indicate that the damage for capillary endothelial cells, following a short incubation of 1 to 2 hours, was maximal and that, at least in a time scale of 24 hours, this damage was non-reversible.

Example 3

Inhibition of Endothelial Cells by Thiram is via Apoptosis

To determine whether the non-reversible inhibition of capillary endothelial cells was induced by the programmed cell death pathway, apoptosis in BCE cells was examined by means of the FACS analysis and by the TUNEL method.

Figure 4:
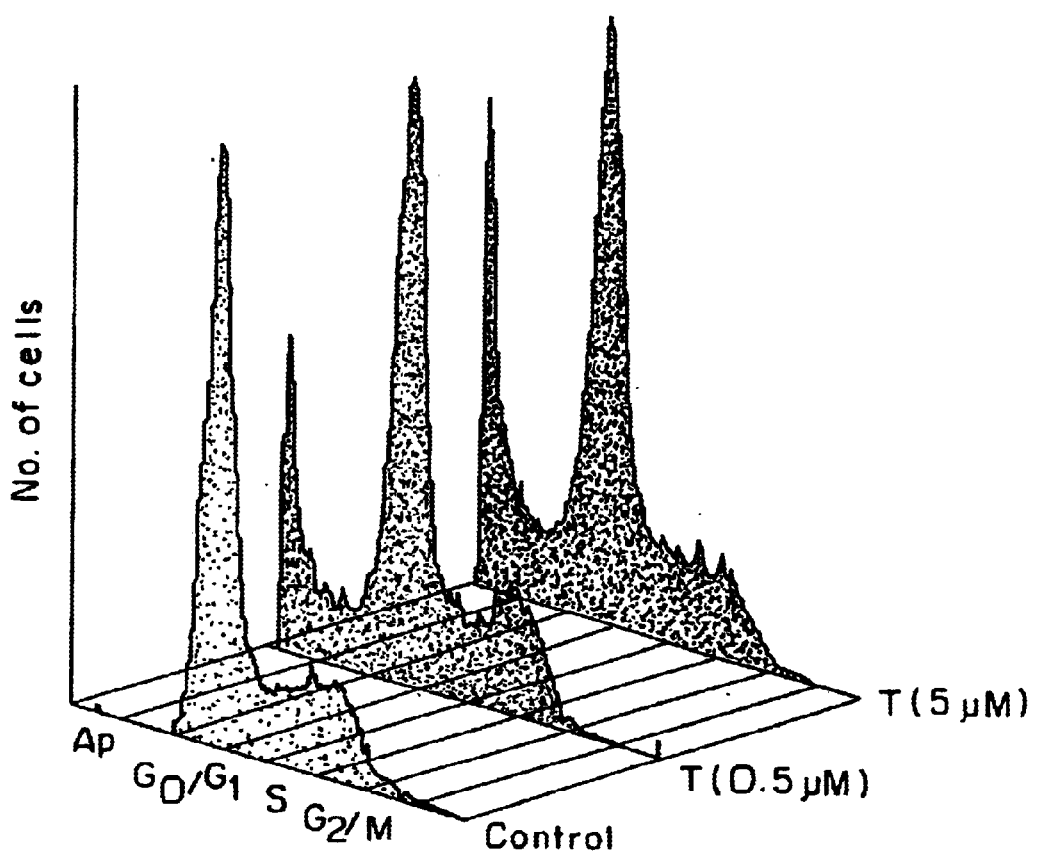
FIG. 4 shows thiram-induced apoptosis in endothelial cells. BCE cells were incubated with 0.5–5 $\mu$M thiram (T) for 20 hours and analyzed by FACS for the DNA content of the cells. Thiram induced in a dose-dependent manner a sub-diploid apoptotic population of endothelial cells, that was not apparent in control-treated cells. Experiments were repeated twice with triplicates.

BCE cells were grown during 48 hours to 40–50% confluency and thiram was then added to the cells for 20 hours as described in section (f) of Materials and Methods above. The results are shown in FIG. 4. FACS analysis of the DNA content of BCE cells incubated with 0.5–5 μM thiram demonstrated the appearance of a sub-diploid apoptotic population of cells. The abundance of apoptotic cells was dose-dependent. In contrast, control non-treated endothelial cells did not undergo this DNA degradation process and most of the cells were in the $G_0/G_1$ phase and some in the S and $G_2/M$ phase. Unlike BCE cells, BALB/MK keratinocytes treated with 4 μM thiram and analyzed by FACS, did not exhibit induction of apoptosis (not shown). Typically for cells undergoing apoptosis, endothelial cells treated with thiram quickly became rounded. In contrast, 3T3 fibroblasts, C6 glioma cells or BSMC treated with 1 μM, 2 μM or 5 μM thiram, respectively, did not change their shape to the rounded form.

Figure 5A:
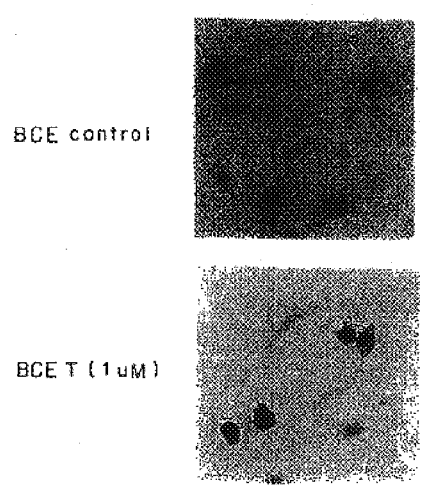
FIGS. 5A–5B show thiram-induced apoptosis in BCE, BSMC, C6 glioma and BALB/MK cells, following incubation with the indicated concentrations of thiram (T) (6 hours for BCE, BSMC and C6 glioma cells and 20 hours for BALB/MK cells), as analyzed by the TUNEL method. The nuclei of BCE cells (FIG. 5A, bottom) treated with thiram were labeled using the TUNEL staining method, while the nuclei of control BCE (FIG. 5A, top) and of BSMC (FIG. 5B, top), MK (FIG. 5B, middle) and C6 glioma cells (FIG. 5B, bottom) treated with thiram were not labeled using the TUNEL staining method. Experiments were repeated twice with triplicates.
Figure 5B:
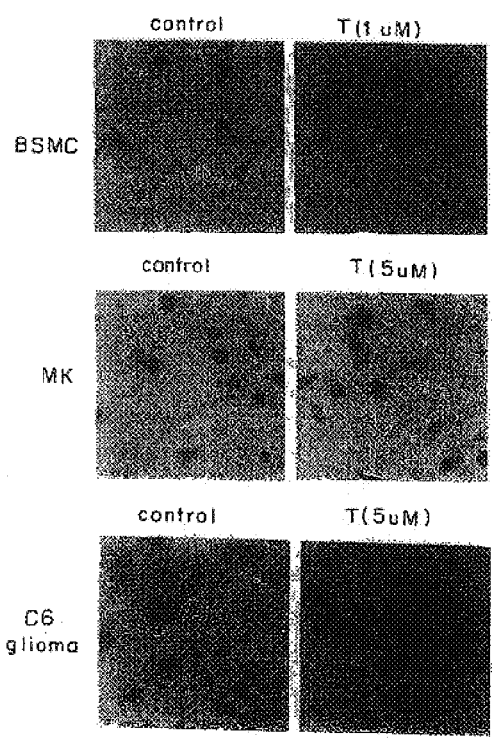

The TUNEL method was used to label the nuclei of cells undergoing apoptosis as described in section (g) of Materials and Methods above. The results are shown in FIG. 5. Capillary endothelial (BCE) cells incubated for 6 hours with 1 μM thiram were induced into apoptosis (FIG. 5A, bottom). In contrast, thiram did not induce BSMC (1 μM) (FIG. 5B, top), BALB/MK keratinocytes (5 μM) (FIG. 5B, middle) and C6 rat glioma cells (5 μM) (FIG. 5B, bottom) into apoptosis following incubation for 6 hours, as measured by the TUNEL method. Capillary endothelial cells are, thus, distinct in their apparent sensitivity to the thiram-induced apoptosis.

Example 4

Thiram Inhibits C6 Glioma Tumor Growth in vivo

Since thiram was shown to be an effective inhibitor of neovascularization in vivo as well as inhibitory to C6 glioma cell growth in vitro, it was expected that systemic treatment with the drug may slow tumor development, since active angiogenesis is essential for the progressive growth of solid tumors beyond a diameter of a few millimeters (Folkman, 1990). The effect of thiram was examined in a C6 rat glioma model in CD1 nude mice using concentrations that were shown to be inhibitory for angiogenesis in vivo. Tumors from mice fed systemically 3 times a week with thiram (T) were weighed 30 days following administration of C6 rat glioma cells to CD1 nude mice. The growth of the tumors was significantly retarded by systemic treatment by thiram. Compared with water-fed control, tumors from animals treated with thiram were significantly smaller. Experiments were repeated twice (n=8).

As shown in Table 1, at thiram concentrations of 25–120 µg/mouse, tumor development was retarded by 58–42%, respectively. Interestingly, the most effective concentration was the lowest one. This is in agreement with the data observed that thiram became less inhibitory for in vitro cell growth at high concentration (not shown). Since thiram inhibits angiogenesis both in vivo in mice and in vitro in C6 glioma cells, it can be assumed that the tumor growth inhibition observed by thiram may be the result of its dual action, one on the neovascularization of the tumor and one on the C6 glioma cells. Pathological examination of various tissues (kidney, liver, stomach, lungs and spleen), including histological sections prepared from these tissues, revealed no effect on these tissues in the treated animals. Blood vessels examined in these tissues were also not affected.

TABLE 1

Thiram inhibits C6 rat glioma tumor growth in nude mice

|          | (n) | Tumor weight (g)[a] | % inhibition | p value[b] |
|----------|-----|---------------------|--------------|------------|
| Control  | (8) | 1.37 ± 0.21         | 0            |            |
| T (25 µg)| (8) | 0.57 ± 0.12         | 58           | p = 0.004  |
| T (120 µg)| (8)| 0.79 ± 0.21         | 42           | p = 0.04   |

[a]Tumors were weighed 30 days following administration of C6 rat glioma cells into nude mice.
Indicated values are mean of (n) animals ± SEM.
[b]Significance of difference between control and treated animals as determined by Student's test.

Example 5

Thiram Inhibits Lewis Lung Metastasis in the i.v. Model

Figure 6:
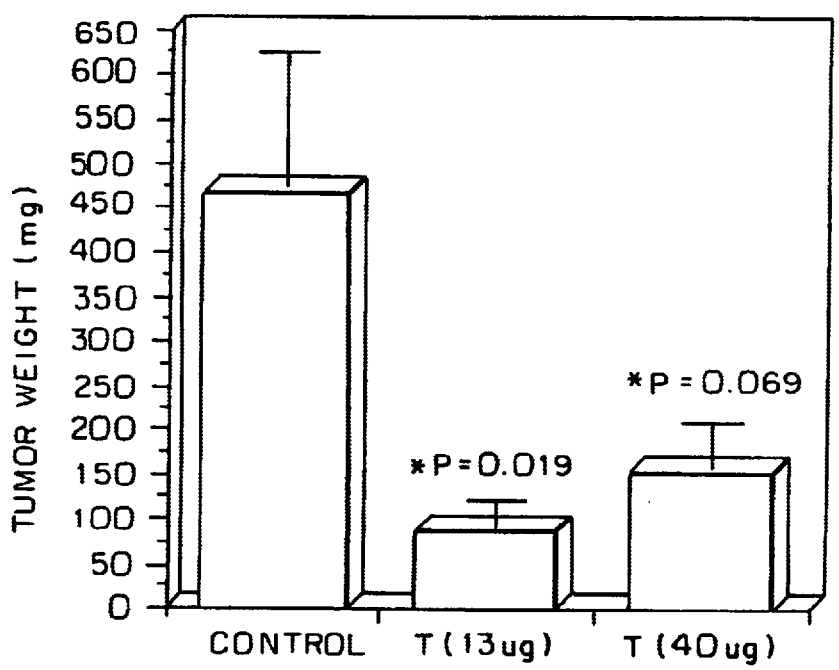
FIG. 6 shows that thiram inhibits Lewis lung tumor metastasis into the lungs of mice in the i.v. model. Lungs from C57/BL mice fed systemically 3 times a week with thiram (13–40 $\mu$g) were weighed 24 days following injection of D122 tumor cells i.v. The weight of the lungs from normal mice was subtracted from that of the metastasized lungs. Compared with water-fed control, metastasis in the lungs of thiram-treated animals was significantly smaller (n=6) (p=0.019–0.069). At 13 $\mu$g/mouse, thiram decreased 6 fold the metastasis in the lungs. Experiments were repeated twice.

To examine the effect of thiram on the development of a tumor from a metastatic foci, the i.v. model was used as described in section (h) of Materials and Methods above. Three days following D122 cell i.v. injection, thiram was administered per os 3 times per week, at concentrations of 13–40 µg/mouse. As shown in FIG. 6, thiram inhibited 70–83% of the development of metastatic foci in the lungs. The highly inhibitory effec of thiram to lung metastasis in the i.v. model indicates that the inhibitory effect takes place during foci development.

Example 6

Thiram Decreases Inflammation in the Adjuvant Arthritis Model

Figure 7:
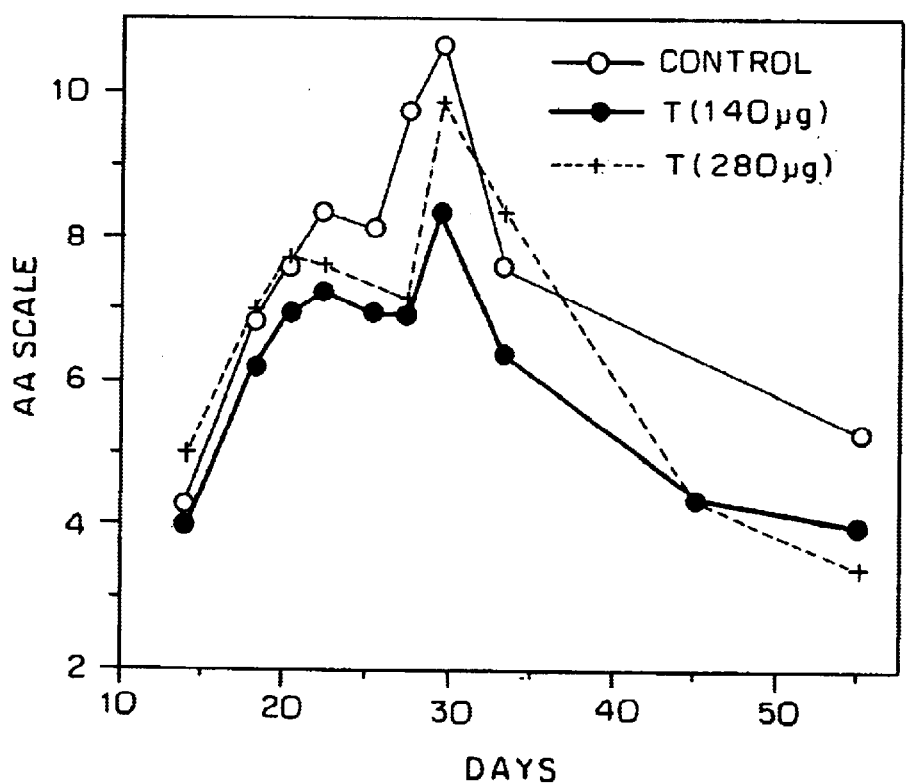
FIG. 7 shows that thiram decreases the inflammatory response in rats with adjuvant arthrithis (AA). Thiram was administered per os three times a week at concentrations of 140 (black circles) and 280 (crosses) $\mu$g/rat. Rats treated with 140 $\mu$g/rat of thiram demonstrated a much reduced inflammatory response along the examination period.

Since inflammation is normally accompanied by increased blood vessel formation we have assumed that an agent capable of inhibiting angiogenesis may also decrease inflammation. The adjuvant arthrithis (AA) model was chosen to examine the effect of thiram on the severity of the inflammatory response. Adjuvant arthritis was induced in Lewis rats as described in section (i) of Materials and Methods. Thiram was administered per os to rats, three times per week at concentrations of 140–280 µg/rat, starting 3 days after the MT injection. The results are shown in FIG. 7. Rats treated with 140 µg thiram/rat showed a much reduced inflammatory response during the examination period in comparison to the control non-treated rats.

References

1. Abramovitch, R., Meir, G., and Neeman, M. (1995). Neovascularization induced growth of implanted C6 glioma multicellular spheroids: magnetic resonance microimaging. Cancer Res 55, 1956–62.
2. Afanasyev, V. N., Korol, B. A., Matylevich, N. P., Pechatnikov, V. A., and Umansky, S. R. (1993). The use of flow cytometry for the investigation of cell death. Cytometry 14, 603–9.
3. Darzynkiewicz, Z., Bruno, S., Del Bino, G., Gorczyca, W., Hotz, M. A., Lassota, P., and Traganos, F. (1992). Features of apoptotic cells measured by flow cytometry. Cytometry 13, 795–808.
4. Eisenbach, L., Segal, S., and Feldman, M. (1983). MHC imbalance and metastatic spread in Lewis lung carcinoma clones. Int. J.Cancer 32, 113–20.
5. Elskens, M. T., and Penninckx, M. J. (1995). In vitro inactivation of yeast glutathione reductase by tetramethylthiuram disulphide. Eur. J. Biochem 231, 667–72.
6. Folkman, J. (1990). What is the evidence that tumors are angiogenesis dependent? J. Natl. Cancer Inst. 82 4–6.
7. Freundt, K. J., and Netz, H. (1977). Behavior of blood acetaldehyde in alcohol-treated rats following administration of thiurams.Arzneimittelforschung 27, 105–8.
8. George, J., and Kuttan, R (1995). Studies on clastogenic and carcinogenic potency of tetramethyl thiuram disulphide. Cancer Lett. 97, 213–6.
9. Hasegawa, R., Takahashi, M., Furukawa, F., Toyoda, K., Sato, H. Jang, J. J., and Hayashi, Y. (1988). Carcinogenicity study of tetramethylthiuram disulfide (thiram) in F344 rats. Toxicology 51, 155–65.
10. Higashiyama, S., Abraham, J. A., Miller, J., Fiddes, J. C., and Klagsbrun, M. (1991). A heparin-binding growth factor secreted by macrophage-like cells that is related to EGF. Science 251 936–9.
11. Ikeda, E., Achen, M. G., Breier, G., and Risau, W. (1995). Hypoxia-induced transcriptional activation and increased mRNA stability of vascular endothelial growth factor in C6 glioma cells. J.Biol. Chem 270, 19761–6.
12. Klimova, A. A. (1990). Expression of heteroorganic antigens—nonhistone chromosomal proteins of renal nature in liver cells of rats after administration of tetramethyl-thiuram disulfide and N-nitrosodiethylamine. Eksp Onkol 12, 76–7.
13. Maita, K., Tsuda, S., and Shirasu, Y. (1991). Chronic toxicity studies with thiram in Wistar rats and beagle dogs. Fundam. Appl. Toxicol 16, 667–86.
14. Marikovsky, M., Vogt P., Eriksson, E., Rubin, J., Taylor, V., Sasse, J. and Klagsbrun, M. (1996). Wound-fluid derived heparin-binding epidermal growth factor (HB-EGF) is synergistic with IGF-1 for BALB/MK keratinocyte proliferation. J. Investig. Dermatology 106, 616–621.
15. Niida, H., Takeuchi, S., Tanaka, R., and Minakawa, T. (1995). Angiogenesis in microvascular endothelial cells induced by glioma cells and inhibited by tumor necrosis factor in vitro. Neurol. Med. Chir.Tokvo 35, 209–14.

16. Pearson, C. M. (1956). Development of arthritis, periarthritis and periostitis in rats given adjuvant. Proc. Soc. Exp. Biol. Med. 91, 91.
17. Pearson, C. M. (1964). Experimental models in rheumatoid diseases. Arthritis Rheum. 7, 80.
18. Perocco, P., Santucci, M. A., Campani, A. G., and Forti, G. C. (1989). Toxic and DNA-damaging activities of the fungicides mancozeb and thiram (TMTD) on human lymphocytes in vitro. Teratog Carcinog Mutagen 9, 75–81.
19. Plate, K. H., Breier, G., Weich, H. A., and Risau, W. (1992). Vascular endothelial growth factor is a potential tumour angiogenesis factor in human gliomas in vivo. Nature 359 845–848.
20. Sadurska, B., and Boguszewski, B. (1993). Changes in lipoprotein lipase activity and plasma liver lipids in thiram intoxicated rats. Acta Biochim Pol 40, 563–7.
21. Sanny, C. G., and Weiner, H. (1987). Inactivation of horse liver mitochondrial aldehyde dehydrogenase by disulfiram. Evidence that disulfiram is not an active-site-directed reagent. Biochem. J. 242 499–503.
22. Takahashi, M., Kokubo, T., Furukawa, F., Nagano, K., Maekawa, A., Kurokawa, Y., and Hayashi, Y. (1983). Inhibition of spontaneous leukemia in F-344 rats by tetramethylthiuram disulfide (thiram). Gann 74, 810–3.
23. Wride, M. A., Lapchak, P. H., and Sanders, E. J. (1994). Distribution of TNF alpha-like proteins correlates with some regions of programmed cell death in the chick embryo. Int. J. Dev. Biol. 38, 673–82.

What is claimed is:

1. A method for inhibiting angiogenesis and/or inflammation in an individual which comprises administering to an individual in need thereof an amount of thiram effective for inhibiting angiogenesis and/or inflammation.

2. The method according to claim 1, for the treatment of an angiogenesis-dependent disease.

3. The method according to claim 2, wherein said angiogenesis-dependent disease is selected from the group consisting of an ophthalmologic, a dermatologic, a pediatric, a connective tissue or a neurologic cerebrovascular disorder, a neoplasm consisting of a leukemia or a solid tumor selected from the group consisting of bladder, breast, cervix, ear, esophagus, kidney, larynx, liver, lung, ovary, pancreas, prostate, skin, stomach, thyroid, urethra and uterus cancers, and hypertrophic scars.

4. The method according to claim 3, wherein the ophthalmologic disorder is diabetic retinopathy, corneal graft neovascularization, neovascular glaucoma, trachoma, or retrolental fibroplasia.

5. The method according to claim 3, wherein the dermatologic disorder is dermatitis or pyogenic granuloma.

6. The method according to claim 3, wherein the pediatric disorder is hemangioma, angiofibroma or hemophilic joints.

7. The method according to claim 3, wherein the connective tissue disorder is scleroderma.

8. The method according to claim 3, wherein the neurologic cerebrovascular disorder is arteriovenous malformation.

9. The method according to claim 1, for the inhibition, alleviation or treatment of inflammatory symptoms associated with rheumatic diseases.

10. The method according to claim 9, for the inhibition, alleviation or treatment of inflammatory symptoms associated with rheumatic fever and rheumatoid arthritis.

11. The method according to claim 1, for the inhibition, alleviation or treatment of inflammatory symptoms associated with fibrositis, myositis, neuritis, sciatica, lumbago, glomerulitis, nephritis, vasculitis, allergic diseases and autoimmune diseases.

12. The method according to claim 1 wherein thiram is administered orally.

13. A method for inhibiting cell hyperproliferation along or around a medical device which comprises coating the device with thiram prior to its insertion into a patient.

14. The method according to claim 13 wherein said medical device is a stent, catheter, cannula, or an electrode.

* * * * *